United States Patent
Jackson et al.

(10) Patent No.: US 8,844,077 B2
(45) Date of Patent: Sep. 30, 2014

(54) SYNCRONIZED PATIENT ELEVATION AND POSITIONING APPARATUS POSITIONING SUPPORT SYSTEMS

(71) Applicants: Roger P. Jackson, Prairie Village, KS (US); Lawrence E. Guerra, Mission, KS (US); Michael A. Herron, Overland Park, KS (US)

(72) Inventors: Roger P. Jackson, Prairie Village, KS (US); Lawrence E. Guerra, Mission, KS (US); Michael A. Herron, Overland Park, KS (US)

( * ) Notice: Subject to any disclaimer, the term of this patent is extended or adjusted under 35 U.S.C. 154(b) by 0 days.

(21) Appl. No.: 13/955,707

(22) Filed: Jul. 31, 2013

(65) Prior Publication Data

US 2013/0312182 A1  Nov. 28, 2013

Related U.S. Application Data

(63) Continuation-in-part of application No. 13/317,012, filed on Oct. 6, 2011, now Pat. No. 8,719,979, which is a continuation of application No. 12/460,702, filed on Jul. 23, 2009, now Pat. No. 8,060,960, and a continuation of application No. 11/788,513, filed on Apr. 20, 2007, now Pat. No. 7,565,708, which is a continuation-in-part of application No. 11/159,494, filed on Jun. 23, 2005, now Pat. No. 7,343,635, which is a continuation-in-part of application No. 11/062,775, filed on Feb. 22, 2005, now Pat. No. 7,152,261.

(60) Provisional application No. 61/742,167, filed on Aug. 3, 2012, provisional application No. 60/798,288, filed on May 5, 2006.

(51) Int. Cl.
| | | |
|---|---|---|
| A61G 13/04 | (2006.01) | |
| A61G 7/008 | (2006.01) | |
| A61B 6/04 | (2006.01) | |
| A61G 13/00 | (2006.01) | |
| A61G 7/00 | (2006.01) | |
| A61G 13/08 | (2006.01) | |
| A61G 7/012 | (2006.01) | |

(52) U.S. Cl.
CPC .............. *A61G 7/001* (2013.01); *A61G 7/008* (2013.01); *A61B 6/0407* (2013.01); *A61G 13/0036* (2013.01); *A61G 2013/0054* (2013.01); *A61G 2210/10* (2013.01); *A61G 7/012* (2013.01); *A61G 13/08* (2013.01); *A61G 13/04* (2013.01); *A61G 2200/327* (2013.01); *A61G 2200/325* (2013.01)
USPC ........................................ 5/607; 5/610; 5/611

(58) Field of Classification Search
CPC .............................. A61G 13/04; A61G 7/001
USPC .............. 5/607, 608, 610, 611, 613, 617, 618
See application file for complete search history.

(56) References Cited

U.S. PATENT DOCUMENTS

| 1,938,006 A | 12/1933 | Blanchard | |
|---|---|---|---|
| 2,188,592 A * | 1/1940 | Hosken et al. | .................... 5/607 |

(Continued)

FOREIGN PATENT DOCUMENTS

| GB | 569758 | 6/1945 |
|---|---|---|
| GB | 810956 | 3/1959 |

(Continued)

OTHER PUBLICATIONS

Brochure of OSI on Modular Table System 90D, pp. 1-15, date of first publication: Unknow.

(Continued)

*Primary Examiner* — Michael Trettel
(74) *Attorney, Agent, or Firm* — John C. McMahon

(57) ABSTRACT

An apparatus for transferring a supine patient to a prone position on a patient positioning support system, and for rotating such a prone patient between prone and supine positions without removing the patient from the patient positioning support system.

13 Claims, 6 Drawing Sheets

(56) References Cited

U.S. PATENT DOCUMENTS

| | | |
|---|---|---|
| 2,261,297 A | 11/1941 | Frederick |
| 2,636,793 A | 4/1953 | Meyer |
| 3,046,071 A | 7/1962 | Shampaine et al. |
| 3,049,726 A * | 8/1962 | Getz ............... 5/86.1 |
| 3,281,141 A | 10/1966 | Smiley et al. |
| 3,584,321 A | 6/1971 | Buchanan |
| 3,599,964 A | 8/1971 | Magni |
| 3,766,384 A | 10/1973 | Anderson |
| 3,814,414 A | 6/1974 | Chapa |
| 4,101,120 A | 7/1978 | Seshima |
| 4,131,802 A | 12/1978 | Braden et al. |
| 4,144,880 A | 3/1979 | Daniels |
| 4,148,472 A | 4/1979 | Rais et al. |
| 4,175,550 A | 11/1979 | Leininger et al. |
| 4,186,917 A | 2/1980 | Rais et al. |
| 4,227,269 A | 10/1980 | Johnston |
| 4,503,844 A | 3/1985 | Siczek |
| 4,552,346 A | 11/1985 | Schnelle et al. |
| 4,712,781 A | 12/1987 | Watanabe |
| 4,763,643 A | 8/1988 | Vrzalik |
| 4,872,657 A | 10/1989 | Lussi |
| 4,937,901 A | 7/1990 | Brennan |
| 4,970,737 A | 11/1990 | Sagel |
| 5,088,706 A * | 2/1992 | Jackson ............... 5/608 |
| 5,131,106 A * | 7/1992 | Jackson ............... 5/613 |
| 5,210,888 A | 5/1993 | Canfield |
| 5,231,741 A | 8/1993 | Maguire |
| 5,239,716 A | 8/1993 | Fisk |
| 5,393,018 A | 2/1995 | Roth et al. |
| 5,444,882 A | 8/1995 | Andrews et al. |
| 5,579,550 A | 12/1996 | Bathrick |
| 5,588,705 A | 12/1996 | Chang |
| 5,658,315 A | 8/1997 | Lamb et al. |
| 6,260,220 B1 | 7/2001 | Lamb et al. |
| 6,295,671 B1 | 10/2001 | Reesby et al. |
| 6,438,777 B1 | 8/2002 | Bender |
| 6,505,365 B1 | 1/2003 | Hanson et al. |
| 6,526,610 B1 | 3/2003 | Hand et al. |
| 6,634,043 B2 | 10/2003 | Lamb et al. |
| 6,638,299 B2 | 10/2003 | Cox |
| 6,681,423 B2 | 1/2004 | Zachrisson |
| 6,701,553 B1 | 3/2004 | Hand et al. |
| 6,971,997 B1 | 12/2005 | Ryan et al. |
| 7,089,612 B2 | 8/2006 | Rocher et al. |
| 7,137,160 B2 | 11/2006 | Hand et al. |
| 7,171,709 B2 | 2/2007 | Weismiller |
| 7,197,778 B2 * | 4/2007 | Sharps ............... 5/81.1 R |
| 7,565,708 B2 * | 7/2009 | Jackson ............... 5/611 |
| 8,381,331 B2 * | 2/2013 | Sharps et al. ............... 5/86.1 |
| 2001/0037524 A1 | 11/2001 | Truwit |
| 2002/0023298 A1 | 2/2002 | Lamb et al. |
| 2003/0055456 A1 | 3/2003 | Cox |
| 2003/0074735 A1 | 4/2003 | Zachrisson |
| 2004/0098804 A1 | 5/2004 | Varadharajulu et al. |
| 2004/0133983 A1 | 7/2004 | Newkirk et al. |
| 2006/0016010 A1 | 1/2006 | Weismiller |
| 2006/0080777 A1 | 4/2006 | Rocher et al. |
| 2006/0123546 A1 | 6/2006 | Horton et al. |
| 2006/0185090 A1 | 8/2006 | Jackson |
| 2007/0107126 A1 | 5/2007 | Koch et al. |
| 2007/0192960 A1 | 8/2007 | Jackson |
| 2008/0000028 A1 | 1/2008 | Lemire et al. |
| 2009/0126116 A1 | 5/2009 | Lamb et al. |
| 2011/0099716 A1 | 5/2011 | Jackson |
| 2011/0107516 A1 | 5/2011 | Jackson |
| 2012/0255122 A1 | 10/2012 | Diel et al. |

FOREIGN PATENT DOCUMENTS

| | | |
|---|---|---|
| JP | S53763 | 1/1978 |
| JP | 2000060995 | 2/2000 |
| WO | 9907320 | 2/1999 |
| WO | 0062731 | 10/2000 |
| WO | WO 00/62731 | 10/2000 |
| WO | 0160308 | 8/2001 |
| WO | 03070145 | 8/2003 |
| WO | 2009054969 | 4/2009 |
| WO | 2009100692 | 8/2009 |

OTHER PUBLICATIONS

Brochure of Smith & Nephew on Spinal Positioning System, 2003, 2004.

Pages from website http://www.schaerermayfieldusa.com, pp. 1-5, date of first publication: Unknown.

* cited by examiner

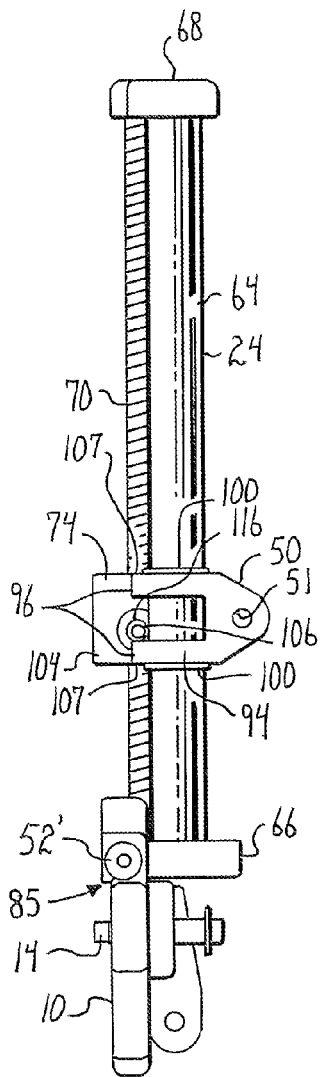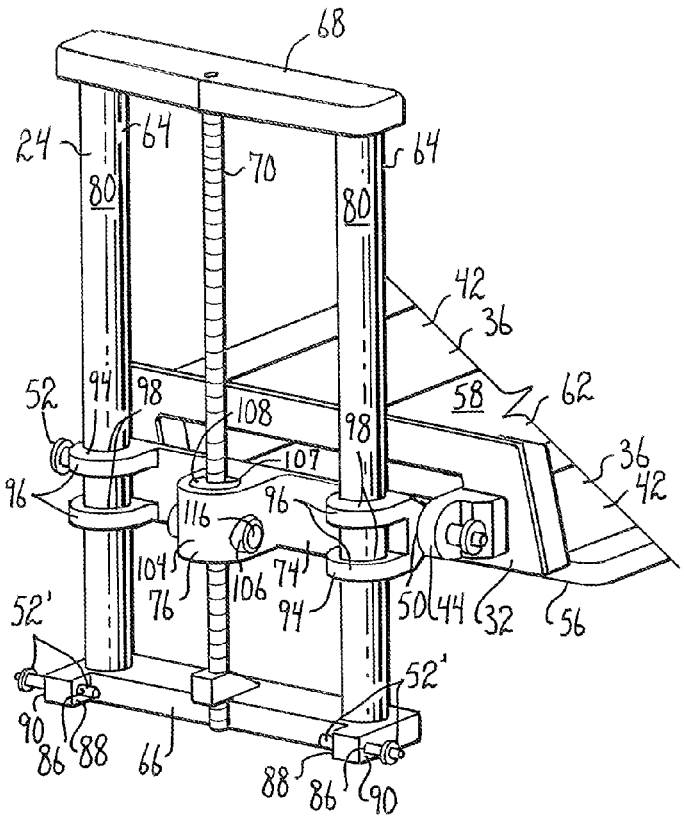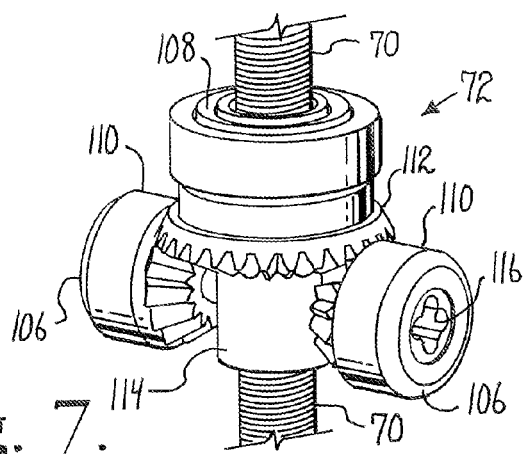
Fig. 5.
Fig. 6.
Fig. 7.

SYNCRONIZED PATIENT ELEVATION AND POSITIONING APPARATUS POSITIONING SUPPORT SYSTEMS

CROSS-REFERENCE TO RELATED APPLICATIONS

This application claims the benefit of U.S. Provisional Application No. 61/742,167 filed Aug. 3, 2012 and entitled "Synchronized Patient Elevation And Positioning Apparatus For Use With Patient Positioning Support Systems," the entirety of which is incorporated by reference herein.

This application is also a Continuation-In-Part of U.S. patent application Ser. No. 13/317,012, now U.S. Pat. No. 8,719,979, which is a Continuation of U.S. patent application Ser. No. 12/460,702, now U.S. Pat. No. 8,060,960, and also which is a Continuation of U.S. patent application Ser. No. 11/788,513, now U.S. Pat. No. 7,565,708, the entirety of which are incorporated by reference herein.

U.S. patent application Ser. No. 11/788,513 claims the benefit of U.S. Provisional Application No. 60/798,288, and is also a Continuation-In-Part of U.S. patent application Ser. No. 11/159,494, now U.S. Pat. No. 7,343,635, which is a Continuation-In-Part of U.S. patent application Ser. No. 11/062,775, now U.S. Pat. No. 7,152,261 the entirety of which are incorporated by reference herein.

BACKGROUND OF THE INVENTION

The present invention is directed to a patient elevation and positioning apparatus for positioning a patient on a patient support structure, such as a surgical table, for a medical procedure. In particular, the present invention is directed to an apparatus for performing a "sandwich and roll" procedure while transferring a patient in a supine position from a bed, gurney or trolley to a prone position on the surgical table.

Certain surgical procedures require changing a patient's body position during said procedure. For example, spinal surgery may require rolling the patient over from a prone position to a supine position, and vice versa. When a standard surgical table is used, rolling the patient over or taking a radiograph often requires transferring the patient between the surgical table and another support, and then back again. Such transfer procedures interrupt the surgical procedure, are cumbersome, and may compromise the surgical site.

Some modern surgical tables, such as modular, multi-articulated patient positioning support systems, have been developed for supporting the patient in a variety of positions and for moving the patient's body in various ways during a surgical procedure, including bending or articulating the patient at the hips, placing the patient in Trendelenburg and reverse-Trendelenburg positions, tilting the patient, and rolling the patient over. Such patient positioning support systems typically include a base with a pair of independently adjustable telescoping support columns that are connected by and support an articulatable patient support structure or table top. The patient support structure may be raised and lowered, and rotated with respect to any of the longitudinal, transverse and vertical axes, so as to be tilted about one or more of the transverse axes, and so as to be rolled about the longitudinal axis in both horizontal and tilted orientations. During some surgeries, a traditional closed patient support structure is replaced with an open frame patient support structure that allows the patient's abdomen to depend therethrough.

U.S. Pat. No. 7,152,261 to Jackson, incorporated herein by reference in its entirety, describes a closed frame modular, multi-articulated patient positioning support system with independently adjustable head- and foot-end telescoping risers, which support a patient support structure that can be raised, lowered and rolled about a longitudinal axis in various horizontal and tilted orientations. A secondary elevator enables lowering the patient support structure foot end to near the floor. A patient placed on the patient support structure can be rolled 180° after installation of a stationary riser and an auxiliary table top that sandwiches the patient against the patient support structure.

U.S. Pat. No. 7,565,708 to Jackson, incorporated herein by reference in its entirety, describes an infinitely adjustable patient positioning support system with and open frame patient support structure that can be articulated or angulated with respect to a centrally-located transverse axis, as well as being raised, lowered and rolled about the longitudinal axis in various horizontal and tilted orientations. An table top structure may be attached to and spaced from the patient support structure, for rolling the patient 180°, however, the distance between the patient support structure and the table top structure must be adjusted manually.

Prior to a surgical procedure, a patient is usually anaesthetized and then place of the patient support structure. Since the patient begins in a supine position on a gurney, also referred to as a trolley or a stretcher, and must be transferred to a prone position on an open frame patient support structure, such positioning procedures can be quite difficult. Accordingly, there is a need for an apparatus for positioning a patient on a patient positioning support structure in the prone position.

SUMMARY OF THE INVENTION

In a first embodiment of the present invention, a patient elevation and positioning apparatus is provided for performing a "sandwich and roll" procedure while positioning a patient in a prone position on a patient positioning support system. Generally, a patient positioning support system is a surgical table having a base with spaced head-end and foot-end elevator subassemblies that removably supports an attached patient support structure that can be rolled about a longitudinal axis, of the patient positioning support system, a distance of up to at least about ±180°. The patient support structure includes either a traditional closed table top or an open frame that allows the patient's abdomen to depend therethrough. The patient elevation and positioning apparatus includes head-end and foot-end lift subassemblies that are removably attached to the ends of a transfer table structure. The head-end and foot-end lift subassemblies are attached to the patient positioning support system head-end and foot-end elevator subassemblies, respectively, such that the transfer table structure is spaced from the patient support structure. Each lift apparatus includes a gear mechanism, with a lead nut that engages a lead screw, for moving the transfer table structure toward and away from the patient support structure. An actuator synchronizes the lift subassemblies, so as to maintain the transfer table structure in a substantially level orientation, relative to the longitudinal axis or to the floor.

In a further embodiment of the patient elevation and positioning apparatus, the transfer table structure includes a frame joined with a tabletop member. The frame includes a pair of spaced support beams joined by head-end and foot-end cross-beams, and cross-beam brackets for releasable hinged attachment to the head-end and foot-end lift subassemblies, respectively. Quick-release pins hingedly join the brackets of the transfer table structure with the respective lift subassemblies.

In another further embodiment of the patient elevation and positioning apparatus, additional quick release pins removably attach the head-end and foot-end lift subassemblies to the respective head-end and foot-end elevator subassemblies.

In yet another further embodiment of the patient elevation and positioning apparatus, each of the lift subassemblies includes a pair of spaced support members; a lead screw spaced from and substantially parallel with the support members; first and second brace members, the first brace member joining a first end of each of the support members and the lead screw and the second brace member joining the second ends of each of the support members and the lead screw, the first brace member including an attachment structure for removable attachment to a respective support subassembly; and a carrier member slidably engaging the support members. The carrier member includes a gear subassembly and a bracket. The gear subassembly operably engages the lead screw so as to move the carrier member in a direction selected from toward and away from the first brace member, or toward and away from the longitudinal roll axis. The bracket releasably hingeably attaches the carrier member and the associated lift subassembly to the transfer table structure.

In a still further embodiment of the patient elevation and positioning apparatus, the lead screw is an ACME screw.

In another further embodiment of the patient elevation and positioning apparatus, the gear subassembly includes a lead nut that rotatably engages the lead screw, and a motor connector for operable engagement of an external motor.

In still another further embodiment of the patient elevation and positioning apparatus, the carrier member includes a pair of sliding brackets, each of which is sized and shaped to slidably engage a support member. In a further embodiment, a bushing is located between each sliding bracket and a respective support member.

In a second embodiment of the invention, a method of transferring a patient to a medical patient positioning support system in a prone position is provided, wherein the patient positioning support system includes a base with spaced head-end and foot-end elevator subassemblies, a patient support structure removably attached to and supported by the elevator subassemblies, and a rotation mechanism for rotating the patient support structure about a longitudinally extending roll axis a distance of up to at least 180°. The method includes the steps of providing a patient elevation and positioning apparatus having head-end and foot-end lift subassemblies and a transfer table structure; releasably attaching the patient elevation and positioning apparatus to the patient positioning support system; orienting the patient elevation and positioning apparatus for patient transfer; placing a patient on the transfer table structure in a supine position; actuating the head-end and foot-end lift subassemblies so as to move the patient toward the patient support structure, such that the patient is snugly sandwiched between the transfer table structure and the patient support structure; rotating the patient positioning support system to the first position, such that the patient supported by the patient support structure in a prone position; and detaching the patient elevation and positioning apparatus from the patient positioning support system.

In a further embodiment, the step of releasably attaching the patient elevation and positioning apparatus to the patient positioning support system includes attaching the head-end lift subassembly to the head-end support subassembly; attaching the foot-end lift subassembly to both the foot-end support subassembly; and attaching the transfer table structure to the head end and foot-end lift subassemblies.

In another further embodiment, the step of orienting the patient elevation and positioning apparatus for patient transfer includes rotating the patient positioning support system from a first position about 180° about the roll axis such that the transfer table structure is located below the patient support structure.

In another further embodiment, the step of actuating the head-end and foot-end lift subassemblies includes actuating a gear subassembly so as to rotate a lead nut relative to a lead screw.

Various objects and advantages of this invention will become apparent from the following description taken in relation to the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 5 is an enlarged perspective view of the outboard side of the foot end of the patient elevation and positioning apparatus of FIG. 1, with portions broken away.

FIG. 6 is an enlarged side view of the foot end subassembly of the patient elevation and positioning apparatus of FIG. 5, wherein the patient elevation and positioning apparatus is attached to a portion of a head end of a patient positioning support system.

FIG. 7 is an enlarged perspective view of a gear mechanism of the foot end lift subassembly of FIG. 6.

DETAILED DESCRIPTION OF THE ILLUSTRATED EMBODIMENTS

Figure 1:
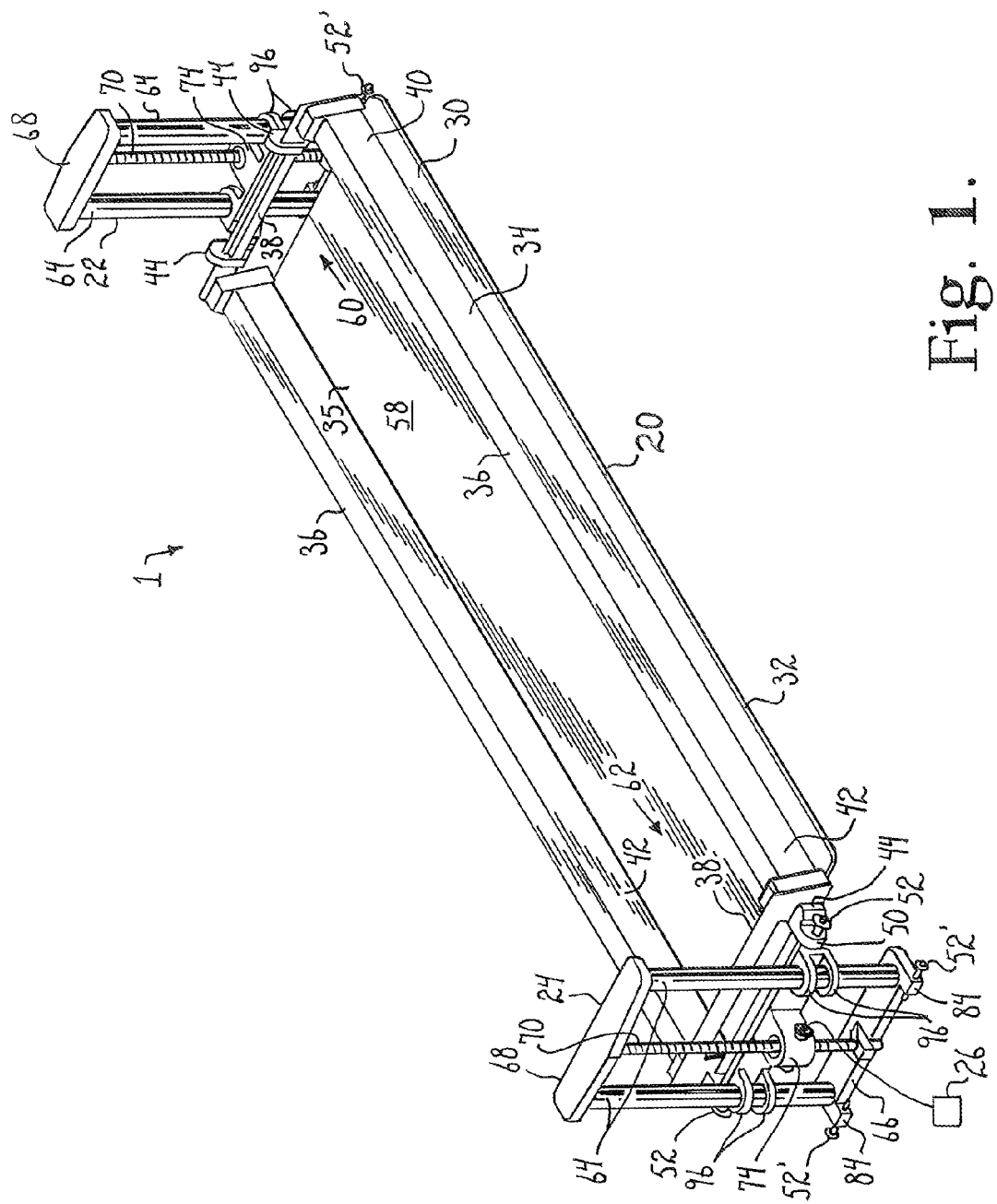
FIG. 1 is a perspective view of a patient elevation and positioning apparatus in accordance with the invention.
Figure 3:
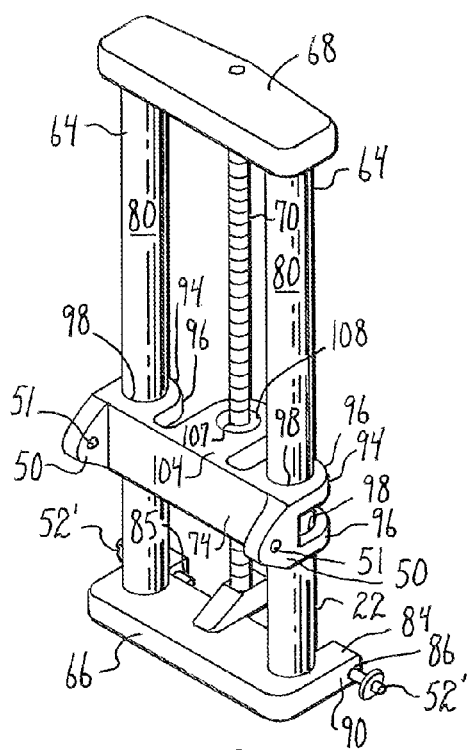
FIG. 3 is a perspective view of the inboard side of the head end subassembly of the patient elevation and positioning apparatus of FIG. 2.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Overview

Referring now to the drawings, a patient elevation and positioning apparatus of the present invention is generally denoted by the numeral 1. The patient elevation and positioning apparatus is useful for positioning a patient 2 in a prone position on a patient positioning support system 4, or surgical table, such as for a medical procedure. An exemplary patient positioning support system 4 is shown in FIGS. 8-13 and is described below.

Patient Positioning Support Systems

The exemplary patient positioning support system 4 depicted in FIGS. 8-13 is a fully adjustable, multi-articulatable and rotatable surgical table that is used during a variety of surgical procedures that require one or more of: rolling the patient between supine and prone positions, bending the patient at the hips, placing the patient in a Trendelenburg or reverse-Trendelenburg position, and moving the patient among various tilted, rolled and angulated positions. Such surgical procedures include but are not limited to orthopedic and spinal surgical procedures. The illustrated patient positioning support system 4 includes a base 6 with spaced opposed outer head-end and foot-end elevator subassemblies 8 and 10, respectively, an elongate patient support structure 12 removably attached to and supported on both ends by a connections structure 14 between the base outer support subassemblies 8, 10 and the elongate patient support structure 12, and a sliding member 16. In some circumstances, the support subassemblies may also be referred to as elevator subassemblies. As is known in the art, in some circumstances, an open patient support structure 12 can be replaced with a traditional closed table top or an imaging table top.

The support subassemblies 8, 10 each include at least one primary elevator adapted for adjusting the height of the attached end of the patient support structure 12 relative to the floor, such as by raising and lowering said attached end. In some embodiments, at least one of the support subassemblies 8, 10 also includes a secondary elevator, and optionally a tertiary elevator. Such height adjustment may be motorized, non-motorized, or a combination thereof, such as is known in the art. Numerous support subassemblies 8, 10 are foreseen.

The connecting structure 14 releasably joins the adjacent end of the patient support structure 12 with the respective adjacent patient support subassembly 8 or 10. The connection structure 14 can be either active or passive, or a combination thereof. For example, an active connection structure 14 is able to resist a bending moment, and may be cantilevered. Further, such an active connection structure 14 may be motorized and optionally synchronized with other portions of the surgical table. If the connection structure 14 is partially or wholly passive, then said passive portions may be manually adjustable. Numerous connection structures 14 are foreseen.

One or both of the connecting structures 14 includes at least one structure, or mechanism, for providing three degrees of movement or freedom of the patient support structure 12 relative to at least one of the support subassemblies 8, 10 and additionally or alternatively relative to the floor. These three degrees of freedom include rotation, pivot or angulation, and yaw, each of which is described in greater detail below.

Figure 9:
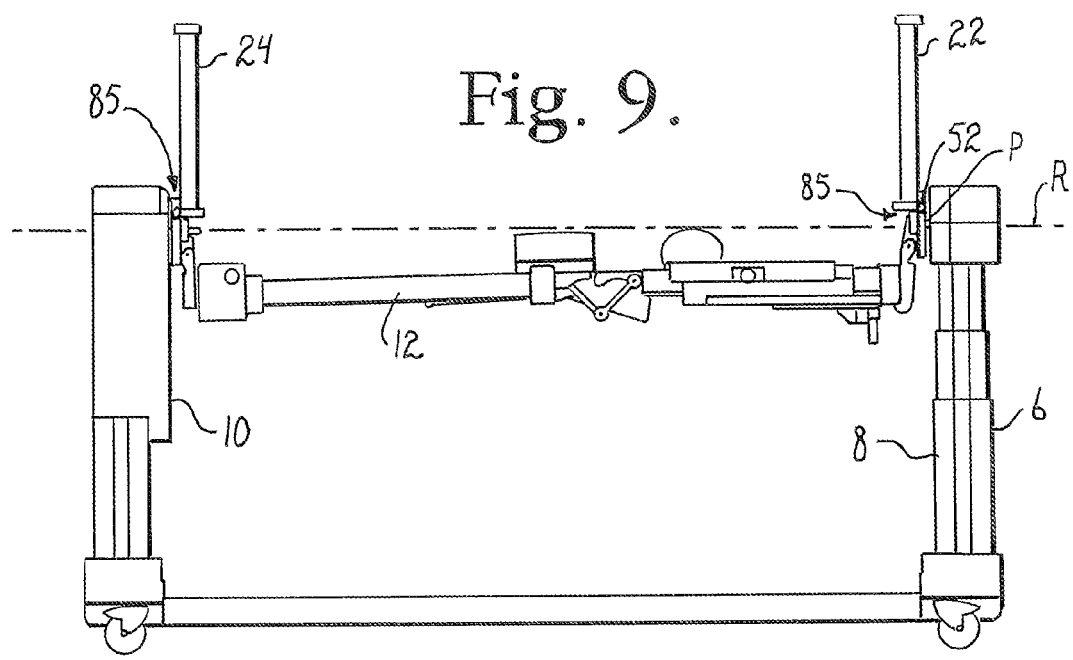
FIG. 9 is a side view of the patient positioning support system of FIG. 8, with head-end and foot-end lift subassemblies of the patient elevation and positioning apparatus attached thereto.

Rotation is provided by a rotation structure for operably turning over a patient on the patient positioning support system 4. Specifically, such rotation structure rotates or tilts the patient support structure 12 about a roll axis R that extends longitudinally between rotational pivot points P of the patient positioning support system 4. The pivot points P are most easily seen in FIG. 9. The rotation structure advantageously enables infinitely adjustable rotation and rolling of the patient support structure 12 a distance or an amount of up to at least ±180° from a first position, such as is shown in FIG. 9. Such rolling provides improved access to the patient 2, and enables turning the patient 2 over between prone and supine positions, so as to provide surgical access to both the patient's front and back without removing the patient 2 from the patient support structure 12. Some patient positioning support systems 4 are configured such that the patient support structure 12 is rotatable an amount of up to at least 360° in either direction. Alternative rotation structures are foreseen.

Each connecting structure 14 includes a pivot or angulation structure that provides rotation at a pivot axis associated with the connection or attachment between the connecting structure 14 and the patient support structure 12. These pivot axes may be referred to as first and second pivot axes. Each of the first and second pivot axes is perpendicular to both the roll axis R and a vertical axis of the adjacent support subassembly 8 or 10. The pivot structures may be active, such as but not limited to a hinge driven by a motor or other drive structure, or passive.

In the illustrated embodiments shown in FIGS. 8-13, each pivot structure is an elongate connection pin that is coaxial with one of the first and second pivot axes, and that joins or engages a portion of a connecting structure 14 with an adjacent end of the patient support structure 12, such as is known in the art, whereby the patient support structure 12 is operable to pivot, tilt or angulate, such as but not limited to in a hinge-like manner, about the respective pivot axis relative to the respective adjacent support subassembly 8 or 10 and/or the floor. Alternative pivot structures are foreseen.

At least one of the connecting structures 14 includes a yaw structure adapted for right-ward or left-ward roll or twist about a yaw axis. Suitable yaw structures may be active or passive, and include but are not limited to pivot pins, slots, and universal joints, such as is known in the art. Alternative yaw structures are foreseen.

The patient support structure 12 may be an open frame or closed surgical table, such as is known in the art. The patient support structure 12 can be fixed or it can "break," angulate or articulate, such as about a third pivot axis that is not associated with either of the connecting structures 14. Such a break can be hinged or hingeless. If hinged, the hinge can be actively driven by a motor or other drive structure, or the hinge can be passive. Breaking the patient support structure 12, at a pivot axis near the middle of the patient support structure 12, enables passive flexing and extension of the lumbar spine and surrounding soft tissues of an anesthetized patient in a prone position on the patient support structure 12.

If the break is hingeless, then the connecting structure 14 on one or both ends of the patient support structure 12 must be active, such as but not limited to hydraulic cylinders, cantilevered, and the like. If the break is configured to be a passive hinge, wherein the upper and lower body portions of the patient support structure 12 are physically attached, then the connection structure 14 on at least one end must, again, be active. If the break is configured to be an actively driven hinge, then the connecting structure can be passive. The active hinge can be driven or moved by a force directly working on said hinge, such as but not limited to a cable or cord, a lead screw, a wedge and a worm gear.

An exemplary breaking patient support structure 12 is shown in FIGS. 8-13, and includes open upper and lower body support frames joined by spaced, opposed hinges associated with a patient's hips. When the patient support structure 12 is angulated at the third pivot axis, the upper and lower body support portions define two sides of a triangle. The length of the third side of the triangle is determined by the amount of angulation around the third pivot axis.

The sliding member compensates for changes in the length of the third side of a triangle described above. In the art, such compensation by the sliding member may be referred to as "translation compensation." In some embodiments, the sliding member is located in the base, particularly in the upright support subassemblies 8, 10. Additionally or alternatively, the sliding member may be located, either wholly or in part, in or on the patient support structure 12. For example, the sliding member may be within the patient support structure 12 or attached to it, such as but not limited to underneath it. Such translation compensation may be active, passive, or a combination thereof, such as is known in the art. Numerous sliding member structures are foreseen for operatively achieving such translation compensation.

Numerous patient positioning support systems 4 find use with the patient elevation and positioning apparatus 1 of the present invention, including those described in U.S. Pat. Nos. 7,152,261, 7,343,635, 7,565,708, and 7,739,762, and also U.S. Publication No. 2009-0282614, U.S. patent application Ser. No. 12/803,525, filed on Jun. 22, 2010 and entitled "Surgery Table Apparatus," U.S. patent application Ser. No. 12/803,173, filed on Jun. 21, 2010 and entitled "Patient Positioning Support Structure," U.S. patent application Ser. No. 12/803,192, filed on Sep. 9, 2010 and entitled "Patient Positioning Support Structure," and U.S. patent application Ser. No. 13/317,012, filed on Oct. 6, 2011 and entitled "Patient Positioning Support Structure," all of which are incorporated by reference herein in their entirety.

Patient Elevation And Positioning Apparatus

Referring now to FIGS. 1-7, the patient elevation and positioning apparatus 1 includes a transfer table structure 20 joining a pair of spaced lift subassemblies, such as head-end and foot-end lift subassemblies 22 and 24, and an actuator 26, all of which are described in greater detail below.

As shown in FIG. 9, the head-end and foot-end lift subassemblies 22 and 24 are removably attachable to the head-end and foot-end elevator subassemblies 8 and 10, respectively, of a patient positioning support system 4. For example, the lift subassemblies 22, 24 must be attached to a respective head-end or foot-end connection structure 14. The head-end and foot-end lift subassemblies 22, 24 are also removably attachable to the transfer table structure head and foot ends 30 and 32, respectively. Each of the lift subassemblies 22 and 24 is adapted for moving the transfer table structure 20 in a direction selected from toward and away from the roll axis R. When being moved by the lift subassemblies 22 and 24, the transfer table structure 20 is maintained in a plane substantially parallel to the roll axis R, since the actuator 26 is adapted to synchronously actuate the lift subassemblies 22 and 24, which is discussed in greater detail below. It is foreseen that in some circumstances, the actuator 26 may actuate the lift subassemblies 22, 24 in a non-synchronous manner, such as but not limited to singularly, independently, at different rates, and in different directions.

Figure 2:
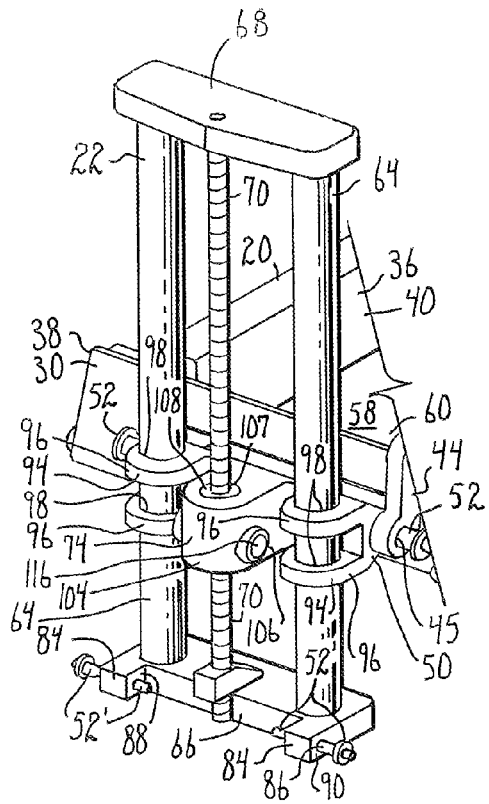
FIG. 2 is an enlarged perspective view of the outboard side of the head end of the patient elevation and positioning apparatus of FIG. 1, with portions broken away.

Referring now to FIGS. 1, 2 and 5, the transfer table structure 20 includes a frame 34 supporting a tabletop member 35. The frame 34 includes a pair of spaced, longitudinally extending support beams 36 joined by cross-beams 38 at their head and foot ends 40 and 42, respectively. The support beams 36 are formed of a material with a high strength-to-weight ratio, with optional radio-transparent properties, such as but not limited to carbon fiber reinforced polymers. Such materials are tough, and resilient but relatively lighter in weight. Such materials enable the surgical staff to handle the transfer table structure 20 without excessive strain thereto, while also enabling the transfer table structure 20 to withstand considerable forces caused by the weight of the patient. Each support beam 36 has a rectangular or trapezoidal cross-section, the cross-section being taken perpendicular to a longitudinal axis of the support beam 36. Such a trapezoidal shape strengthens the support beams 36 and prevents twisting due to stresses applied thereto. However, it is foreseen that the support beams 36 may have a cross-section that is circular, ovular, or any other useful shape known in the art.

The head-end and foot-end cross-beams 38 join the head and foot ends 40, 42 of the spaced support beams 36. Each cross-beam 38 includes a linkage bracket 44 with a substantially cylindrical horizontal channel 45 for releasable hinged attachment to the respective head-end and foot-end lift subassemblies 22, 24, such as described in greater detail below. Preferably, the linkage bracket 44 is a pair of spaced linkage brackets 44 that join the associated cross-beams 38 with the associated lift subassemblies 22, 24, such as is described below.

As shown in FIGS. 1, 2 and 5, the linkage brackets 44 are spaced so as to be engageable by the lift subassemblies 22, 24. Accordingly, the linkage brackets 44 are aligned with engagement brackets 50 of the associated lift subassemblies 22, 24. Each engagement bracket 50 includes a substantially cylindrical horizontal through-bore 51, which is most easily seen in FIGS. 3 and 6. The horizontal through-bores 51 are sized and shaped to receiver therethrough a connection pin, such as but not limited to a quick release pin 52. The each linkage bracket 44 is hingeably attached to a respective aligned engagement bracket 50 by axial alignment of each horizontal channel 45 with an adjacent horizontal through-bore 51, followed by insertion of a spring-loaded quick release pin 52 through the aligned horizontal channel 45 and horizontal through-bore 51. The quick release pins 52 enable the transfer table structure 20 to hingeably pivot with respect to the lift subassemblies 22, 24.

The tabletop member 35 has first and second sides, 56 and 58, respectively, and head- and foot-ends, which are generally denoted by the numerals 60 and 62, respectively. The tabletop member 35 is attached to the support beams 36 and optionally to the cross-beams 38, generally on its second side 58, which may also be referred to as the bottom or lower side. The patient 2 is placed upon the tabletop member first side 56, which may also be referred to as the top or upper side. The tabletop member 35 may be fabricated from any suitable resilient material known in the art, which preferably is at least one of light weight and substantially radio-transparent. In some embodiments, the tabletop member 35 is an imaging table top. It is foreseen that an imaging table may be substituted for the transfer table structure 20.

Referring now to FIGS. 1-7, each of the lift subassemblies includes a pair of spaced cylindrical support members 64 joined by first and second, or upper and lower, brace members 66 and 68, respectively, a lead screw 70, a gear subassembly 72 that engages the lead screw 70, and a carrier member 74 that houses the gear subassembly 72 and includes the engagement brackets 50.

The cylindrical support members 64 are cylindrically shaped solid rods or hollow tubes that extend between the first and second brace members 66 and 68, respectively. As shown in FIGS. 2, 3, 5 and 6, the support members 64 are spaced apart so as to slidingly engage the carrier member 74, which in turn is sized so as to engage either the head end 30 or the foot end 32 of the transfer table structure 20. The support members 64 are fabricated of a resilient and substantially rigid material that provides a substantially smooth surface 80, and preferably is also light weight, such as but not limited to carbon fiber-reinforced polymers.

The lead screw 70 is a power screw that translates turning motion of the gear subassembly 72 into the linear motion, such as upward and downward, of the transfer table structure 20. The lead screw 70 extends between the first and second brace members 66 and 68, and is spaced from and parallel to the support members 64. In some embodiments, the lead screw 70 is an ACME screw with a trapezoidal thread form, which offers high strength and ease of manufacture. In some embodiments, the lead screw includes a non-trapezoidal thread form. In other embodiments, the lead screw is a metric screw. As is discussed in greater detail below, the lead screw 70 engages the gear subassembly 72, which is housed within the carrier member 74. The lead screw 70 is spaced equally from each of the support members 64, so as to balance lifting power transferred through the carrier member 70 to the engagement brackets 50. Consequently, the engagement brackets 50 are moved evenly along the support members 64, with respect to the lead screw 70. Alternative structures for fulfill the function of the lead screw 70 are foreseen.

The first brace member 66 holds a first end of each of the support members 64 and of the lead screw 70 in spaced relation to one another. Additionally, the first brace member 66 joins the associated lift subassembly 22, 24 to a respective patient positioning support system support subassembly 8, 10. Each first brace member 66 includes a pair of spaced connection portions 84 for attaching the lift subassembly 22, 24 to the patient positioning support system 4. In the illustrated embodiment, the connection portions 84 are generally rectangularly prism-shaped and extend outwardly in an outboard direction, so as to be releasably matingly engageable by complementary attachment bracket, generally 85, of the elevator subassemblies 8, 10. However, it is foreseen that the connection portions 84 may have other three-dimensional shapes with a cross-section such as but not limited to circular, ovular, trapezoidal and rectangular.

Each connection portion 84 includes a substantially cylindrical through-bore 86 extending between its inboard and outboard sides 88, 90, respectively. The through-bores 86 are sized and shaped to receiver therethrough a connection pin, such as but not limited to a quick release pin 52'. Thus, a quick release pin 52' extends from the outboard side 90 of each of the connection portion 84, through the associated through-bore 86 and outward to the inboard side 88. When attached to the patient positioning support system 4, each quick release pin 52' also engages an support subassembly attachment bracket 85 that is mated with the associated connection portion 84, so as to hold the mated bracket 85 and connection portion 84 together in a substantially rigid, non-hingeable configuration. In some embodiments, the pair of quick release pins 52' are replaced by a longer pin or rod that extends through both of the through-bores 86. Other attachment structures for attaching the lift subassemblies 22, 24 to the patient positioning support system 4 are foreseen.

The second brace member 68 holds the second ends of the support members 64 and the lead screw 70 in substantially the same spaced relation to one another as does the first brace member 66, such that the support members 64 and the lead screw 70 are oriented, configured or run substantially parallel to one another. In some embodiments, one or more of the support members 64 and the lead screw 70 extend through the second brace member 68. In other embodiments, one or more of the support members 64 and the lead screw 70 do not extend through the second brace member 68.

Referring to FIGS. 1-3 and 5, it is noted that the lift subassemblies 22 and 24 are substantially similar in their appearance, components and construction. However, the relative width of the lift subassemblies 22, 24, such as, for example the spacing between the support members 64, or the width of the brace members 66 and 68, may differ between the head and foot ends, so as to accommodate differences in spacing of the transfer table structure support beams 36 at their head and foot ends, or such differences between the head and foot ends of the patient positioning support system base 6. For example, in the illustrated embodiment, the head-end linkage brackets 44, shown in FIG. 2, are spaced closer together than are the foot-end linkage brackets 44, shown in FIG. 5. Accordingly, in this embodiment, the head-end lift subassembly support members 64 are spaced closer together than the foot-end lift subassembly support members 64. It is foreseen that in some embodiments, the spacing between the support members 64 of both of the head-end and foot-end lift subassemblies 22 and 24 are substantially the same, and that these head-end and foot-end lift subassemblies 22 and 24 may be at least one of mirror images of each other and interchangeable.

The carrier member 74 extends between and slidingly engages both of the support members 64, such that movement of the carrier member 74 is guided by the support members 64. The carrier member 74 is slidingly movable toward or away from the first brace ember 66, with respect to the support member 46. The carrier member 74 includes a pair of ring members 94, wherein a ring member 94 is associated with each of the support members 64. Each ring member 94 includes at least one ring structure 96 with a through-bore 98 through which the associated support member 64 is slidingly received. In the illustrated embodiment, each ring member 94 includes a pair of ring structures 96 that are aligned so as to be coaxial with the associated support member 64. A bushing 100 is located in each of the ring structure through-bores 96. Each of the bushings 100 includes a through-bore that receives a support member 64 therethrough, such that the bushing through-bore and the support member 64 are coaxial. The smooth inner surface of each bushing through-bore provides a bearing surface for linear motion of the associated support member 64.

Each carrier member 74 also includes a housing 104 for the gear subassembly 72, which operably engages the associated lead screw 70. As shown in FIGS. 2, 4, 5 and 7, the housing 104 shrouds the gear subassembly 72 and includes at least one access port 106 for connecting, engaging, or plugging in, the actuator 26, and axially aligned upper and lower screw openings 107 that provide a passageway for the lead screw 70 to pass through, so as to enable the gear subassembly 72 to move upward and downward along the length of the lead screw 70. In some embodiments, a bearing 108, that is sized and shaped to fit between the screw opening 107 and the lead screw 70, constrains motion of the housing 104 relative to the lead screw 70, such as is known in the art. The bearing 108 may be any useful bearing known in the art.

Figure 4:
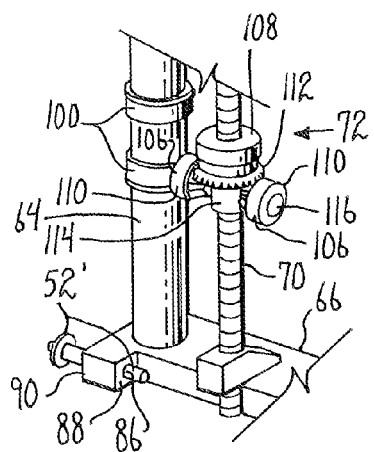
FIG. 4 is a perspective view of the apparatus of FIG. 3, with portions removed to show greater detail of the gear mechanism.

FIGS. 4 and 7 illustrate an exemplary gear subassembly 72 for use with the instant invention. The illustrated gear subassembly 72 includes a gear drive 110 that engages a gear 112 that operably engages a lead nut 114, which is in operable engagement with the lead screw 70. However, it is foreseen that the gear assembly 72 may have any other useful configuration known in the art. The gear drive 110 may be, but is not limited to, a spur, beveled, skewed, helical, hydroploid, double helical or crown gear drive. Similarly, the gear 112 is complementary to and cooperates with the gear drive 110, and may have any useful configuration known in the art, such as but not limited to a spur, beveled, skewed, helical, hydroploid, double helical and crown gears. As shown in FIG. 7, the lead nut 114 is operably engaged by or attached to the gear 112. The lead nut 114 includes a thread (not shown) that is operably complementary to the thread of the lead screw 70. For example, if the lead screw 70 is an ACME screw, then the lead nut 114 is an ACME nut. Alternative screw and nut thread configurations are foreseen.

The drive gear 110 includes a gear engagement portion 116 that is associated with the housing access portion 106. The actuator 26, such as but not limited to an external motor, operably connects with the gear engagement portion 116, so as to actuate, power or drive the gear subassembly 72. In some embodiments, the actuator 26 connects, or plugs, directly to the drive gear 110. In other embodiments, the actuator 26 connects indirectly to the gear engagement portion 116 such as but not limited to by a cord that can be plugged thereinto. Numerous alternative motorized and manual configurations known in the art are foreseen.

Upon actuation by the actuator 26, the gear subassembly 72 engages the lead screw 70 by rotating the lead nut 114 in a clockwise or a counter clockwise direction, so as to rotatingly move the lead nut 114 along the length of the lead screw 70, such that, depending upon the direction of lead nut 114 rotation, the carrier member 74 is moved in a direction selected from toward and away from the first brace member 66, thereby lowering and raising the associated end of an attached transfer table structure 20. For example, the gear drive rotates, causing the rotatingly engaged gear to rotate, such as clockwise or counter clockwise, which in turn causes the lead nut 114 to rotate with respect to the lead screw 70. As is known in the art, such rotation causes the lead nut 114 to rotatingly move up and down the lead screw 70, depending upon the direction of lead nut rotation 114 (e.g., clockwise or counter clockwise).

Referring now to FIGS. 1 and 8-13, the patient elevation and positioning apparatus 1 of the present invention is useful for transferring a patient 2 to a patient positioning support system 4, or surgical table, in a prone position. If the patient 2 is already on the patient positioning support system 4, the patient elevation and positioning apparatus 1 is useful for turning the patient 2 over from a prone position to a supine position, and vice vera.

Referring to FIG. 9, prior to moving the patient 2, the head-end lift subassembly 22 is attached, or installed, to the head-end support subassembly 8, and the foot-end lift subassembly 24 is attached, or installed, to the foot-end support subassembly 10. These attachments are accomplished by engaging the connection portions 84 of the respective first brace members 66 with the attachment brackets 85 of the respective head-end and foot-end elevator subassemblies 8, 10, using quick release pins 52' to maintain said engagements. These engagements are fixed, such that substantially no hingeable pivoting occurs between the engaged attachment brackets 85 and elevator subassemblies 8, 10.

Figure 10:
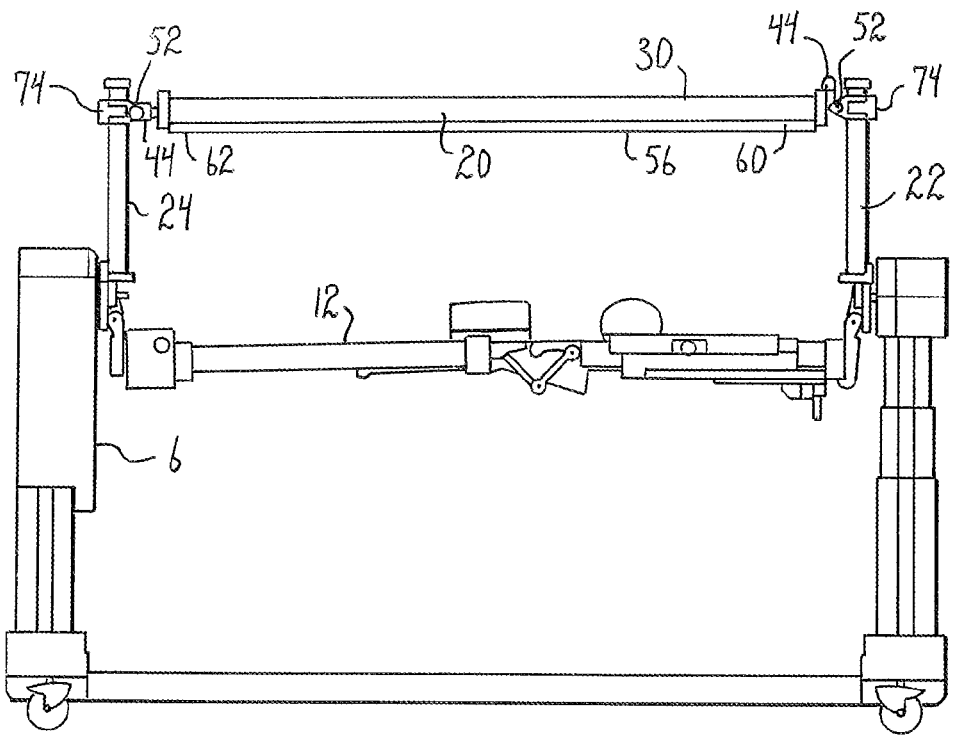
FIG. 10 is a side view of the patient positioning support system of FIG. 9, with a transfer table structure attached to the head-end and foot-end lift subassemblies, wherein the transfer table structure is spaced a maximum distance from the patient support structure.

Next, as shown in FIG. 10, the transfer table structure 20 is attached, or installed, to the head-end and foot-end lift subassemblies 20, 24. This is accomplished by hingeably attaching the linkage brackets 44 of the head end cross-beam 38 to the head-end engagement bracket of the head-end lift subassembly 22; and also hingeably attaching the linkage brackets 44 of the foot end cross-beam 38 to the foot-end engagement bracket of the head-end lift subassembly 24. For example, the horizontal channels 45 of linkage brackets 44 are axially aligned with the engagement bracket horizontal through-bores 51, followed by removable insertion of a quick release pin 52 through each aligned horizontal channel 44 and horizontal through-bore 51 pair.

Figure 11:
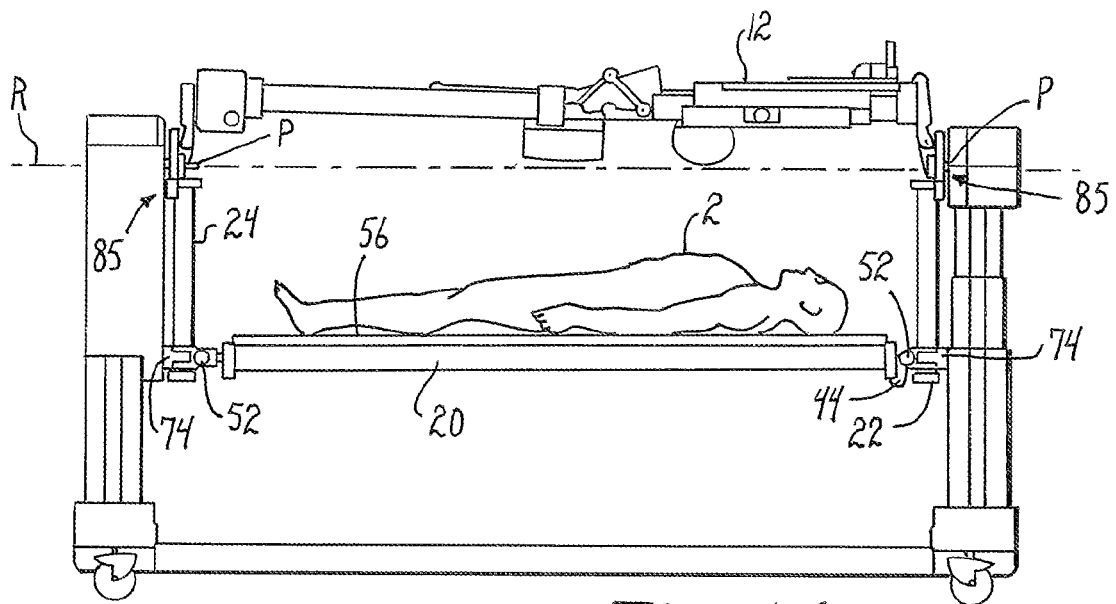
FIG. 11 is a side view of the patient positioning support system of FIG. 10, wherein the patient support structure and the attached patient elevation and positioning apparatus have been rolled approximately 180° with respect to the longitudinal axis, which is denoted by the letter R, and with a patient positioned in a supine position on the transfer table structure.

As shown in FIG. 11, the patient support structure 12 is then rotated about the roll axis R, a distance of approximately 180°, until the transfer table structure 20 is located below the patient support structure 12. The patient 2 can then be moved to the transfer table structure 20 from an adjacent bed or gurney, such that the transfer table structure 20 supports the weight of the patient 2. Generally, the patient 2 is in a supine position, or facing upward, on both the bed and the transfer table structure 20.

Figure 12:
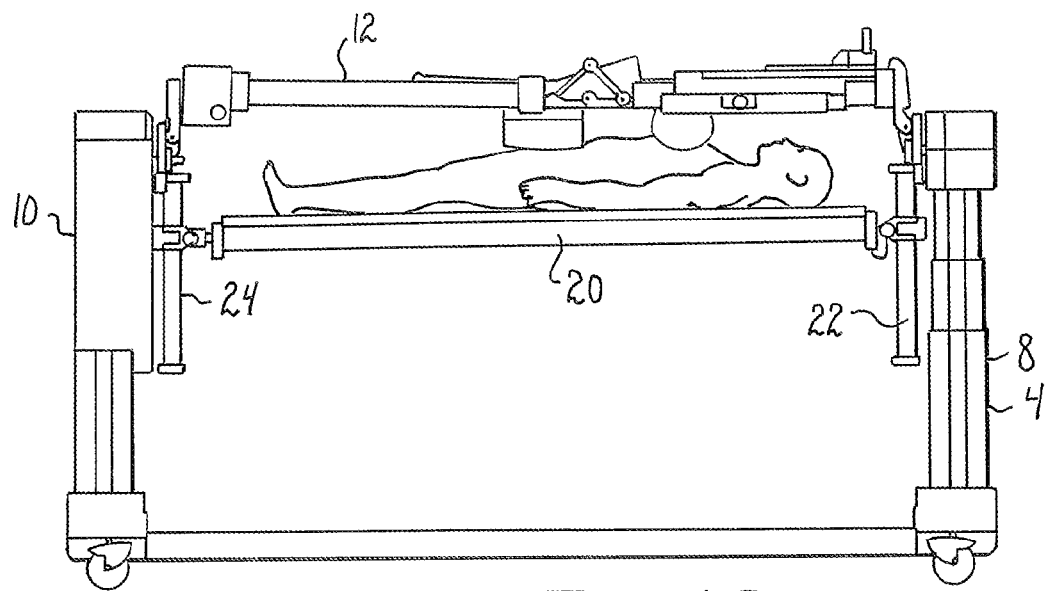
FIG. 12 is a side view of the patient positioning support system of FIG. 11, wherein the head-end and foot-end lift subassemblies have been synchronously actuated to raise the transfer table structure and the patient toward the patient support structure of the patient positioning support system, until the patient is sandwiched between the patient support and transfer table structures.

Next, as shown in FIG. 12, the patient 2 is lifted by the lift subassemblies 22, 24, until the patient 2 is firmly sandwiched between the transfer table structure 20 and the patient support structure 12. Specifically, lifting the patient 2 is accomplished by simultaneously actuating the two gear subassemblies 72, so as to move both the head and foot ends 30, 32 of the transfer table structure 20 toward the rotation axis R at substantially the same rate. In FIG. 12, movement of the transfer table structure 20 toward the rotation axis R appears as movement away from the floor (not shown) that supports the patient positioning support system 4.

In some embodiments, an external actuator 26, or motor, is releasably attached to each of the gear engagement portions 116, and then the lift subassemblies 22, 24 are actuated simultaneously. During actuation, the lead nuts 114 rotate with respect to the engaged lead screws 70, which in turn causes the attached carrier members 74 to move with respect to the support members 64, thereby simultaneously moving the head and foot ends 30, 32 of the attached transfer table structure 20. In some embodiments, the gear subassemblies 72 each include an internal actuator 26. For example, an internal actuator 26 may be housed in each of the carrier members 74. In yet another embodiment, the gear subassemblies 72 are actuated by one or more actuators located in the patient positioning support system 4, such as but not limited to a software synchronization device and/or software.

Figure 13:
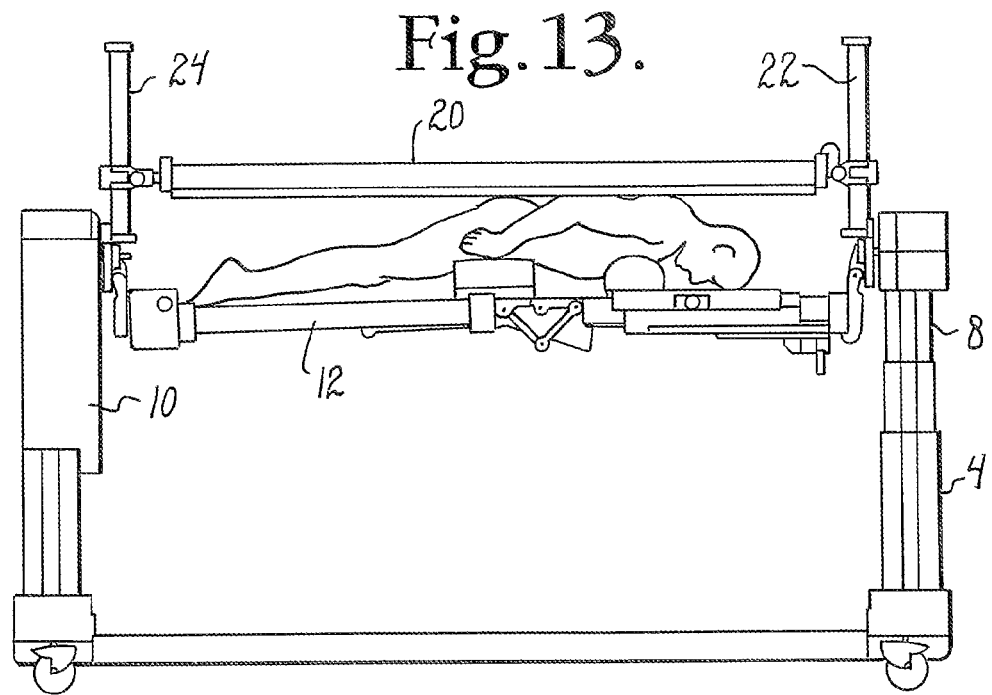
FIG. 13 is a side view of the patient positioning support system of FIG. 10, wherein the patient support structure and patient elevation and positioning apparatus have been rolled back to the starting position, such that the patient rests on the patient support structure in a prone position.

Referring now to FIG. 13, when the patient 2 is sandwiched firmly between the transfer table structure 20 and the patient support structure 12, the patient support structure 12 is again rotated approximately ±180° with respect to the roll axis R, such as, for example, until the patient support structure 12 is located below the transfer table structure 20. During this second rotation, the weight of the patient 2 is transferred from the transfer table structure 20 to the patient support structure 12. When this second rotation is completed, the patient 2 is in a prone, or downwardly facing, position on the patient support structure 12.

Once the patient 2 is supported by the patient support structure 12 of the patient positioning support system 4, the patient elevation and positioning apparatus 1 may be removed from the patient positioning support system 4. Such removal is performed by reversing the installation steps described above. For example, the transfer table structure 20 is lifted a distance above the patient 2 by reversing the actuator 26 and rotating the lead nut 114 with respect to the lead screw 70, such that the patient 2 is no longer sandwiched between the transfer table structure 20 and the patient support structure 12. Then the quick release pins 52 are removed, and the transfer table structure 20 is removed from the lift subassemblies 22, 24. And then the lift subassemblies 22, 24 are removed from the respective elevator subassemblies 8, 10 by disconnection, or removal, of the quick release pins 52'.

Figure 8:
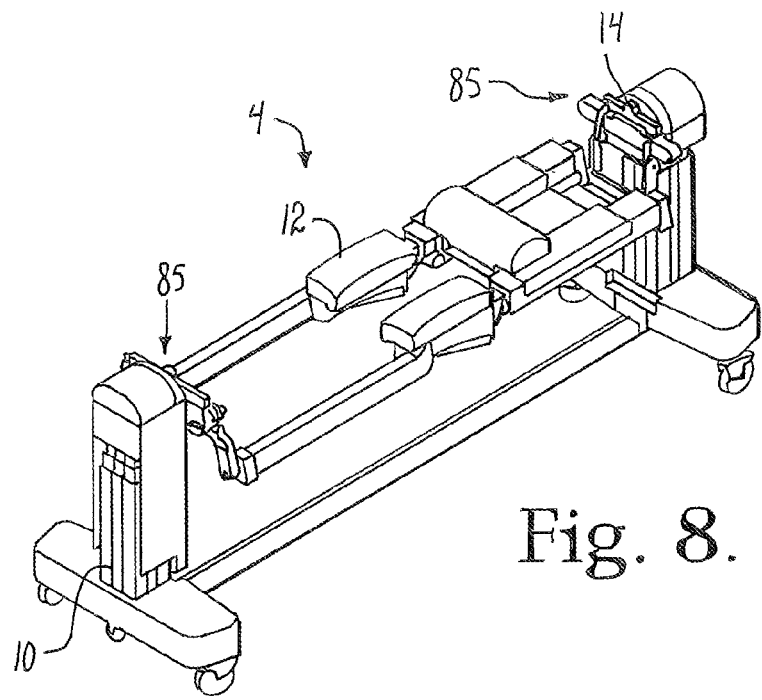
FIG. 8 is a perspective view of an exemplary patient positioning support system, or surgical table, for use with the patient elevation and positioning apparatus of FIG. 1.

In some circumstances, it is desirable to turn a patient 2 over, from a prone position to a supine position, while the patient 2 is supported on the patient support structure 4, such as is shown in FIG. 8. Similar to the procedure described above, the head-end and foot-end lift subassemblies 22, 24 are attached to the respective head-end and foot-end elevator subassemblies 8, 10. The apparatus 1 will appear similar to that shown in FIG. 9, with a patient 2 (not shown) in a prone position on the patient support structure 12. Then, the transfer table structure 20 is attached to the head-end and foot-end lift subassemblies 22, 24. The apparatus 1 will appear similar to what is shown in FIGS. 10 and 13, with a patient 2 (not shown) in a prone position on the patient support structure 12. The transfer table structure 20 will then be lowered until the patient 2 is firmly sandwiched between the transfer table structure 20 and the patient support structure 4. In certain embodiments, an imaging table is used instead of a transfer table structure 20, such that a radiological image of the patient can be taken at this point, or the patient 2 can be rolled over onto the imaging table for such an image. When the patient 2 is firmly sandwiched between the patient support structure 4 and the transfer table structure 20, or an imaging table, the patient support structure 12 is rotated, or rolled, about ±180° with respect to the roll axis R, such as until the patient support structure 12 is located above the transfer table structure 20, such as is shown in FIG. 12. The transfer table structure 20 can then be lowered, such that a radiological image of the patient can be taken or a surgical procedure can be performed on the patient 2 in a supine position, or the patient 2 can be transferred back to a bed or gurney.

It is to be understood that while certain forms of the present invention have been illustrated and described herein, it is not to be limited to the specific forms or arrangement of parts described and shown.

What is claimed and desired to be secured by Letters Patent is as follows:

1. A patient elevation and positioning apparatus for positioning a patient in a prone position on a patient positioning support system for a medical procedure, the patient positioning support system including a base with spaced head-end and foot-end support subassemblies, a patient support structure removably attached to and supported by the support subassemblies, and a rotation mechanism for rotating the patient support structure about a longitudinally extending roll axis a distance of up to at least 180°, the patient elevation and positioning apparatus comprising:
   a) a transfer table structure having head and foot ends, the transfer table structure being sized and shaped for receiving and supporting a patient thereon;
   b) a head-end lift subassembly removably attachable to both the head-end support subassembly and the transfer table structure head end, the head-end lift subassembly being adapted for moving the transfer table structure head end in a direction selected from toward and away from the roll axis;
   c) a foot-end lift subassembly removably attachable to both the foot-end support subassembly and the transfer table structure foot end, the foot-end lift subassembly being adapted for moving the transfer table structure foot end in a direction selected from toward and away from the roll axis; and
   d) an actuator for synchronously actuating the head-end and foot-end lift subassemblies, so as to maintain the transfer table structure in a plane substantially parallel to the roll axis while moving the transfer table structure in a direction selected from toward and away from the roll axis.

2. The apparatus according to claim 1, the transfer table structure comprising:
   a) a pair of spaced support beams, each beam having a foot end and a head end;
   b) a head-end cross-beam joining the head ends of the spaced support beams, the head-end cross-beam including a bracket for releasable hinged attachment to the head-end lift subassembly;
   c) a foot-end cross-beam joining the foot ends of the spaced support beams, the foot-end cross-beam including a bracket for releasable attachment to the foot-end lift subassembly; and
   d) a tabletop member attached to the support beams.

3. The apparatus according to claim 1, further comprising:
   a) a plurality of quick release pins sized and shaped for removably attaching at least one of the head-end lift subassembly and the foot-end lift subassembly to at least one of a respective support subassembly and a respective transfer table structure end.

4. The apparatus according to claim 1, each of the lift subassemblies comprising:
   a) a pair of spaced support members;
   b) a lead screw spaced from and substantially parallel with the support members;
   c) a first brace member joining a first end of each of the support members and the lead screw, the first brace member including an attachment structure for removable attachment to a respective support subassembly;
   d) a second brace member joining a second end of each of the support members and the jack screw; and
   e) a carrier member slidably engaging the support members, the carrier member having
      i) a gear subassembly operably engaging the lead screw so as to move the carrier member in a direction selected from toward and away from the first brace member, and
      ii) a bracket for releasable hingeable attachment to the transfer table structure.

5. The apparatus according to claim 4, wherein:
   a) the lead screw is an ACME screw.

6. The apparatus according to claim 4, the gear subassembly comprising:
   a) a lead nut rotatably engaging the lead screw; and
   b) a motor connector for operable engagement of an external motor.

7. The apparatus according to claim 4, the carrier member including:
   a) a pair of sliding brackets, each sliding bracket being sized and shaped to slidably engage a support member.

8. The apparatus according to claim 7, wherein;
   b) a bushing is located between each sliding bracket and a respective support member.

9. A method of transferring a patient to a medical patient positioning support system in a prone position, the patient positioning support system including a base with spaced head-end and foot-end elevator subassemblies, a patient support structure removably attached to and supported by the elevator subassemblies, and a rotation mechanism for rotating the patient support structure about a longitudinally extending roll axis a distance of up to at least 180°, the method comprising:
  a) providing a patient elevation and positioning apparatus having head-end and foot-end lift subassemblies and a transfer table structure;
  b) releasably attaching the patient elevation and positioning apparatus to the patient positioning support system;
  e) orienting the patient elevation and positioning apparatus for patient transfer;
  f) placing a patient on the transfer table structure in a supine position;
  g) actuating the head-end and foot-end lift subassemblies so as to move the patient toward the patient support structure, such that the patient is snugly sandwiched between the transfer table structure and the patient support structure;
  h) rotating the patient positioning support system to the first position, such that the patient support structured by the patient support structure in a prone position; and
  i) detaching the patient elevation and positioning apparatus from the patient positioning support system.

10. The method according to claim 9, wherein releasably attaching the patient elevation and positioning apparatus to the patient positioning support system comprises:
  a) attaching the head-end lift subassembly to the head-end support subassembly;
  b) attaching the foot-end lift subassembly to both the foot-end support subassembly; and
  c) attaching the transfer table structure to the head end and foot-end lift subassemblies.

11. The method according to claim 9, wherein orienting the patient elevation and positioning apparatus for patient transfer comprises:
  a) rotating the patient positioning support system from a first position about 180° about the roll axis such that the transfer table structure is located below the patient support structure.

12. The method according to claim 9, wherein actuating the head-end and foot-end lift subassemblies comprises:
  a) actuating a gear subassembly so as to rotate a lead nut relative to a lead screw.

13. A surgical table comprising:
  a) a base having a first patient support structure extending between opposed end supports thereof;
  b) the end supports having attachment structure for a second patient support structure including an actively driven lift subassembly; and
  c) wherein a patient can be positioned between the first and second patient support structure and the distance between the first and second patient support structures is adjustable by the actively driven lift subassembly.

* * * * *